(12) United States Patent
Rocci et al.

(10) Patent No.: US 11,980,406 B2
(45) Date of Patent: May 14, 2024

(54) CORRECTION GUIDE FOR FEMORAL NECK

(71) Applicant: DEPUY SYNTHES PRODUCTS, INC., Raynham, MA (US)

(72) Inventors: Mirko Rocci, Zuchwil (CH); This Aebi, Zuchwil (CH); Martin Oswald, Meilen (CH); David Mueller, Zuchwil (CH); Darko Selkic, Haegendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 486 days.

(21) Appl. No.: 17/249,898

(22) Filed: Mar. 17, 2021

(65) Prior Publication Data

US 2021/0204992 A1    Jul. 8, 2021

Related U.S. Application Data

(63) Continuation of application No. 15/664,664, filed on Jul. 31, 2017, now Pat. No. 10,966,773.

(51) Int. Cl.
| | |
|---|---|
| *A61B 17/88* | (2006.01) |
| *A61B 17/17* | (2006.01) |
| *A61B 17/74* | (2006.01) |
| *A61B 17/84* | (2006.01) |
| *A61B 17/00* | (2006.01) |

(52) U.S. Cl.
CPC ...... *A61B 17/8897* (2013.01); *A61B 17/1721* (2013.01); *A61B 17/1742* (2013.01); *A61B 17/742* (2013.01); *A61B 17/842* (2013.01); *A61B 2017/0042* (2013.01)

(58) Field of Classification Search
CPC .. A61B 17/15–151; A61B 17/154–155; A61B 17/17; A61B 17/74–748; A61B 17/846–848; A61B 17/8897; A61B 17/88
See application file for complete search history.

(56) References Cited

U.S. PATENT DOCUMENTS

| | | | |
|---|---|---|---|
| 2,301,500 | A | 11/1942 | Anderson |
| 2,531,734 | A | 11/1950 | Hopkins |
| 4,037,592 | A | 7/1977 | Kronner |
| 4,333,715 | A | 6/1982 | Kirkley |

(Continued)

FOREIGN PATENT DOCUMENTS

| | | |
|---|---|---|
| EP | 2929845 | 10/2015 |
| JP | 2004016463 | 1/2004 |

(Continued)

*Primary Examiner* — Eduardo C Robert
*Assistant Examiner* — Michelle C Eckman
(74) *Attorney, Agent, or Firm* — Fay Kaplun & Marcin, LLP

(57) ABSTRACT

A device for correcting a placement of a guide wire in a bone includes a body extending from a proximal end to a distal end; a central channel extending through the body from the proximal end to the distal end along a central axis, the central channel sized and shaped to receive a guide wire slidably therein; and a first correction channel extending through the body from the proximal end to the distal end. The first correction channel is sized and shaped to receive a guide wire therein at an angle relative to the central axis of the central axis of the central channel.

25 Claims, 6 Drawing Sheets

(56) References Cited

U.S. PATENT DOCUMENTS

| | | | |
|---|---|---|---|
| 4,383,527 A * | 5/1983 | Asnis | A61B 17/1721 606/96 |
| 4,421,122 A | 12/1983 | Duffy | |
| 4,465,065 A | 8/1984 | Gotfried | |
| 5,053,039 A | 10/1991 | Hofmann et al. | |
| 5,078,719 A | 1/1992 | Schreiber | |
| 5,207,753 A | 5/1993 | Badrinath | |
| 5,246,444 A | 9/1993 | Schreiber | |
| 5,254,119 A | 10/1993 | Schreiber | |
| 5,306,278 A | 4/1994 | Dahl et al. | |
| 5,324,295 A | 6/1994 | Shapiro | |
| 5,417,694 A | 5/1995 | Marik et al. | |
| 5,449,360 A | 9/1995 | Schreiber | |
| 5,766,221 A | 6/1998 | Benderev et al. | |
| RE36,020 E | 12/1998 | Moore et al. | |
| 6,007,535 A | 12/1999 | Rayhack et al. | |
| 6,342,056 B1 | 1/2002 | Mac-Thiong et al. | |
| 8,277,458 B2 | 10/2012 | Schneider | |
| 8,317,862 B2 | 11/2012 | Troger et al. | |
| 8,388,624 B2 | 3/2013 | Ek et al. | |
| 8,491,595 B2 | 7/2013 | Volpi et al. | |
| 8,777,957 B2 | 7/2014 | Marino | |
| 9,119,645 B2 | 9/2015 | Mcbride | |
| 9,149,286 B1 | 10/2015 | Greenhalgh et al. | |
| 9,707,001 B2 * | 7/2017 | Kim | A61B 17/1721 |
| 9,855,063 B2 | 1/2018 | Feibel et al. | |
| 9,883,874 B1 | 2/2018 | Vestgaarden | |
| 10,098,646 B2 | 10/2018 | Ardito et al. | |
| 10,154,868 B2 | 12/2018 | Fallin et al. | |
| 10,159,502 B2 | 12/2018 | Wu et al. | |
| 2003/0004513 A1 * | 1/2003 | Guzman | A61B 1/00154 606/62 |
| 2003/0018340 A1 | 1/2003 | Branch | |
| 2003/0216742 A1 | 11/2003 | Wetzler et al. | |
| 2003/0220651 A1 | 11/2003 | Pusnik et al. | |
| 2004/0082959 A1 | 4/2004 | Hayes et al. | |
| 2006/0052795 A1 | 3/2006 | White | |
| 2006/0058810 A1 | 3/2006 | Wozencroft et al. | |
| 2006/0064087 A1 | 3/2006 | Mirza et al. | |
| 2006/0200160 A1 | 9/2006 | Border et al. | |
| 2006/0271059 A1 | 11/2006 | Reay-Young et al. | |
| 2007/0005067 A1 | 1/2007 | Dross | |
| 2008/0015603 A1 | 1/2008 | Collazo | |
| 2008/0086136 A1 | 4/2008 | Bednar | |
| 2008/0103506 A1 | 5/2008 | Volpi et al. | |
| 2009/0088768 A1 * | 4/2009 | Grant | A61B 17/8897 606/280 |
| 2009/0149707 A1 | 6/2009 | Brannon | |
| 2009/0318924 A1 | 12/2009 | Helenbolt et al. | |
| 2010/0036431 A1 | 2/2010 | Haidukewych | |
| 2011/0054550 A1 | 3/2011 | Metzinger et al. | |
| 2011/0213432 A1 | 9/2011 | Geist et al. | |
| 2012/0123415 A1 | 5/2012 | Vienney et al. | |
| 2012/0253353 A1 | 10/2012 | McBride | |
| 2013/0110120 A1 | 5/2013 | Baroud et al. | |
| 2014/0081281 A1 | 3/2014 | Felder | |
| 2014/0277450 A1 | 9/2014 | Warburton | |
| 2015/0066039 A1 | 3/2015 | Siegal et al. | |
| 2015/0066041 A1 | 3/2015 | Kim et al. | |
| 2015/0157379 A1 * | 6/2015 | Matsuzaki | A61B 17/1796 606/103 |
| 2015/0182267 A1 | 7/2015 | Wolf et al. | |
| 2016/0074049 A1 | 3/2016 | Russell et al. | |
| 2016/0089162 A1 | 3/2016 | Ardito et al. | |
| 2016/0270800 A1 | 9/2016 | Sanders | |
| 2016/0310191 A1 | 10/2016 | Seykora et al. | |
| 2016/0338696 A1 | 11/2016 | Loubens | |
| 2016/0367270 A1 | 12/2016 | Garlock et al. | |
| 2017/0042532 A1 | 2/2017 | Valadez et al. | |
| 2018/0235603 A1 | 8/2018 | Heneveld | |
| 2018/0296244 A1 | 10/2018 | Kim | |
| 2018/0344330 A1 | 12/2018 | Thibodeau et al. | |
| 2019/0029743 A1 | 1/2019 | Rocci et al. | |

FOREIGN PATENT DOCUMENTS

| | | |
|---|---|---|
| JP | 2016-179268 | 10/2016 |
| WO | 2019/027802 | 2/2019 |

* cited by examiner

CORRECTION GUIDE FOR FEMORAL NECK

PRIORITY CLAIM

The present application is a Continuation of U.S. patent application Ser. No. 15/664,664 filed on Jul. 31, 2017, now U.S. Pat. No. 10,966,773. The disclosure of the above application is incorporated herein by reference.

BACKGROUND

Femoral neck fractures may be fixed with implants inserted along an axis of the femoral neck so that the implant extends into the femoral head. The femoral implant may be guided along a guide wire inserted along the axis of the femoral neck. Thus, accurate placement of the guide wire is crucial for optimal fixation of the fracture.

SUMMARY OF THE INVENTION

The present invention relates to a device for correcting a placement of a guide wire in a bone, comprising a body extending from a proximal end to a distal end, a central channel extending through the body from the proximal end to the distal end along a central axis, the central channel sized and shaped to receive a guide wire slidably therein, and a first correction channel extending through the body from the proximal end to the distal end, the first correction channel sized and shaped to receive a guide wire therein at an angle relative to the central axis of the central axis of the central channel.

The present invention also relates to a system for correcting a placement of a guide wire in a bone, comprising a device including a body extending from a proximal end to a distal end, the body tapering from the proximal end to the distal end and including a central channel and a first correction channel extending therethrough from the proximal end to the distal end, a handle portion extending from the proximal end of the body at an angle relative to a longitudinal axis thereof, a first guide wire sized and shaped to be inserted through the central channel, and a second guide wire sized and shaped to be inserted through the first correction channel at an angle relative to a central axis of the central channel.

The present invention also relates to a method for correcting a guide wire placement in a bone, comprising inserting a first guide wire through into a bone, imaging the bone to determine a desired corrected placement of the first guide wire, sliding a device along the first guide wire until a distal end thereof abuts a surface of the bone, the device slid along the first guide wire so that the first guide wire is received within a central channel of the device along a central axis thereof, and inserting a second guide wire through a correction channel of the device, the correction channel permitting insertion of the second guide wire therein along an axis corresponding to the desired corrected placement of the first guide wire, the axis of insertion of the second guide wire being one of angled and parallel to the central axis.

BRIEF DESCRIPTION

DETAILED DESCRIPTION

Figure 1:
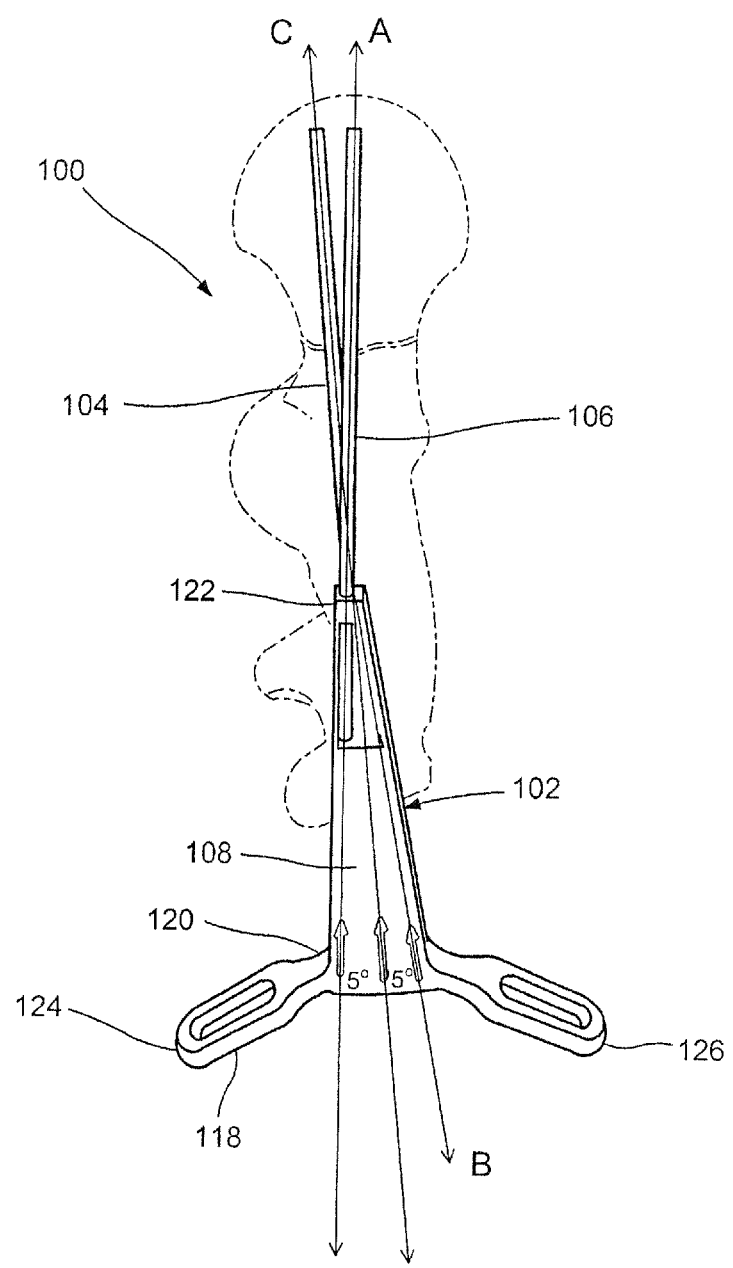
FIG. 1 shows a perspective view of a system according to an exemplary embodiment of the present disclosure, in which first and second guide wires are inserted into a bone at an angle relative to one another.
Figure 2:
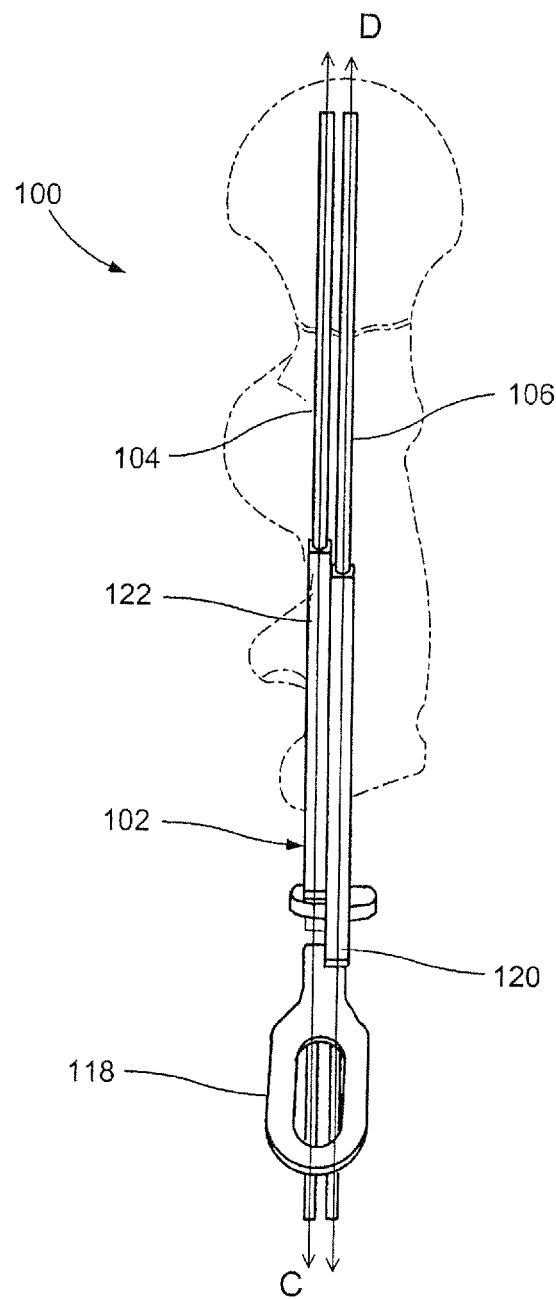
FIG. 2 shows another perspective view of the system of FIG. 1, in which first and second guide wires are inserted into a bone parallel to one another.
Figure 3:
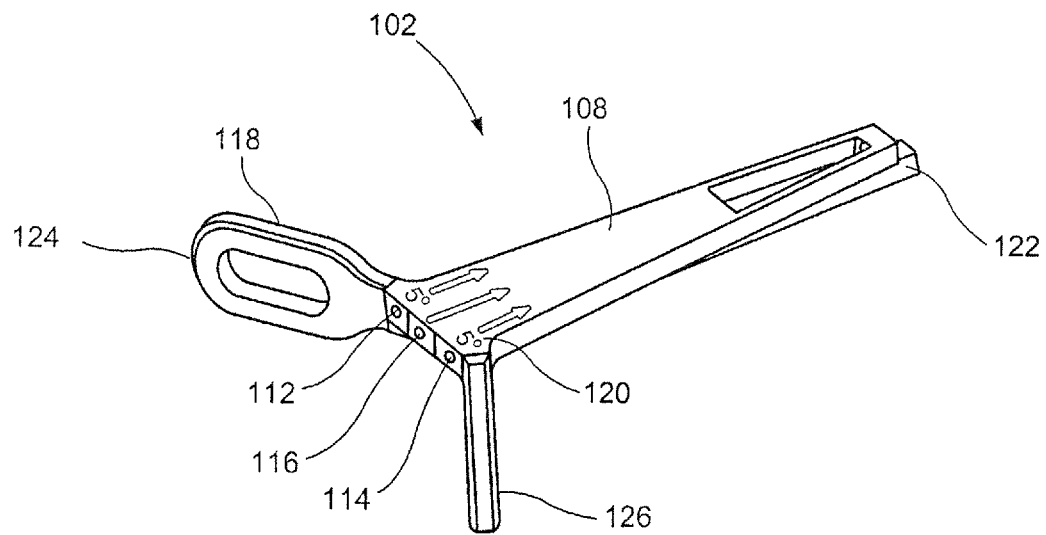
FIG. 3 shows a perspective view of a device of the system of FIG. 1.
Figure 4:
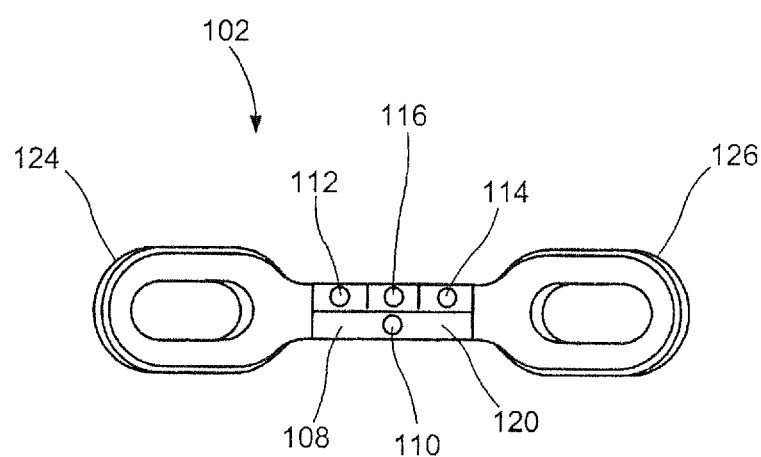
FIG. 4 shows a lateral side view of the device of the system of FIG. 1.
Figure 5:
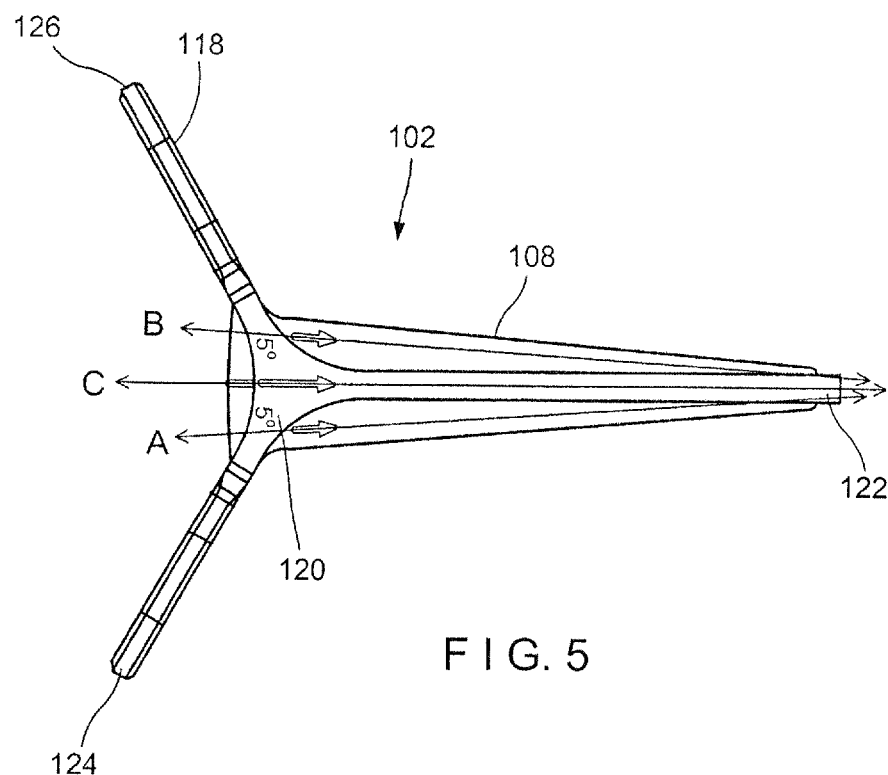
FIG. 5 shows a longitudinal side view of the device of the system of FIG. 1.
Figure 6:
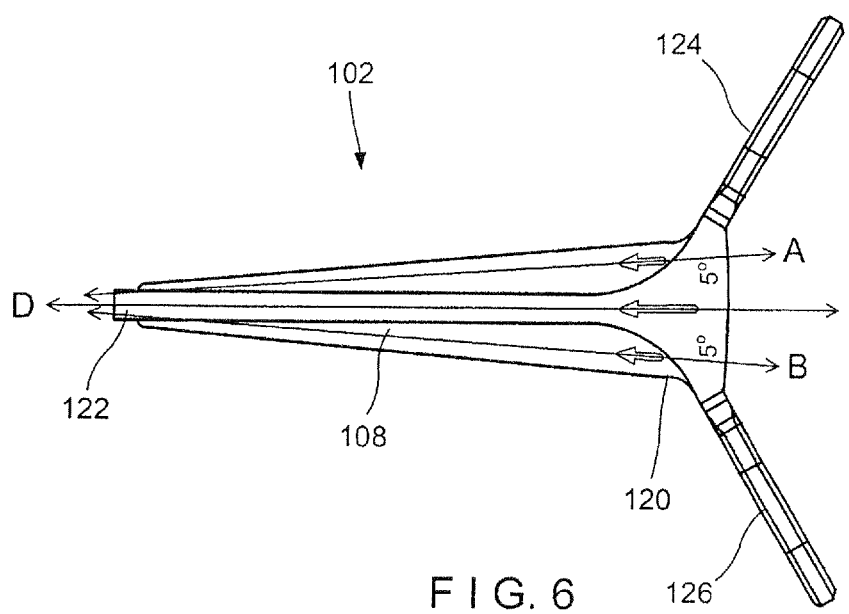
FIG. 6 shows another longitudinal side view of the device of the system of FIG. 1.

The present embodiments may be understood with reference to the following description and the appended drawings, wherein like elements are referred to with the same reference numerals. The present embodiments relate to the treatment of bone fractures and, in particular, relates to the treatment of femoral neck fractures. Exemplary embodiments describe a device for correcting an axis along which a guide wire is inserted into a femoral neck. In particular, when used for guiding femoral neck implants, guide wires should generally be inserted along a central axis of the femoral neck and into the femoral head. In many cases, however, surgeons insert the guide wire into the femoral head without the use of a guiding device, so that an initial placement of the guide wire may require correction. Even with the use of instruments for inserting the guide wire (e.g., an angled guide), correction may be required due to, for example, variances in anatomical structures between patients. Although the exemplary embodiments describe the device as being used for guide wires inserted through the femoral neck, it will be understood by those of skill in the art that the device may be used to correct placement of guide wires inserted in any of a variety of bones. For example, the exemplary device may also be used to correct guide wires placed in the distal femur, proximal humerus, distal humerus and for guide wire placement during foot surgeries. It should be noted that the terms "proximal" and "distal" as used herein, are intended to refer to a direction toward (proximal) and away from (distal) a user (e.g., surgeon) of the device.

As shown in FIGS. 1-4, a system 100 for correcting a position of a guide wire according to an exemplary embodiment of the present disclosure, comprises a correction device 102 for correcting the placement of a first guide wire 104 in a bone (e.g., femoral neck) by inserting a second guide wire 106 either at an angle or parallel the first guide wire 104. The device 102 comprises a body 108 including a central channel 110 for receiving the first guide wire 104 and a first correction channel 112 extending therethrough at an angle relative to the central channel 110. The body 108 may additionally include a second correction channel 114 extending therethrough at an angle relative to the central channel 110 and along a side of the body 108 substantially opposing the first correction channel 112. Each of the first and second correction channels 112, 114 is sized and shaped to receive the second guide wire 106 so that, when the first guide wire 104 is received in the central channel 110, the user may insert the second guide wire 106 through one of the first and second correction channels 112, 114 depending on which correction channel aligns with the axis along which it is desired to insert the second guide wire 106. A third correction channel 116 extends through the body 108 substantially parallel to the first correction channel 110 for use when the user has determined that the second guide wire 116 should extend parallel to the first guide wire 104 but offset laterally from the first guide wire 104. The device 102 additionally includes a handle portion 118 extending from the body 108 to facilitate gripping of the device 102. In use, once it is determined that the placement of the first guide wire 104 should be corrected, the device 102 may be slid along the first guide wire 104 while the first guide wire 104 is received within the central channel 110. Depending on a desired corrected position of the guide wire, the second guide wire 106 is then inserted through one of the first, second and third channels 112, 114, 116 and into the bone. If the second guide wire 106 is in the desired corrected position (e.g., along a central axis of the femoral neck), the first guide wire 104 and the device 102 may be removed, leaving the second guide wire 106.

The body 108 of the device 102 extends from a proximal end 120 to a distal end 122. The central channel 110 extends through the body 108 from the proximal end 120 to the distal end 122 along a central axis C. The first correction channel 112 extends through the body 108 from the proximal end 120 to the distal end 122 along a first axis A, which extends at an angle relative to the central axis C. The first axis A and the central axis C intersect at a point distal of the distal end 122. The second correction channel 114 extends through the body 108 from the proximal end 120 to the distal end 122 along a side of the body 108 substantially opposing the first correction channel 112. The second correction channel 114 extends through the body 108 along an axis B, which extends at an angle relative to the central axis C so that the axes B and C intersect at a point distal of the distal end 122. The body 108 may be marked to show the angulation of each of the first, second and third correction channels 112, 114, 116 relative to the central axis C. In one exemplary embodiment, each of the first and second axes A and B are angled at an angle of 5° relative to the central axis C. It will be understood by those of skill in the art, however, that the angle of the axes A and B relative to the central axis C may vary depending on a desired level of correction of the guide wire. In an exemplary embodiment, the axes A and B may be angled relative to the central axis C by an angle up to 20°. It will also be understood by those of skill in the art that the first axis A and the second axis B may have angulations that are different from one another.

The third correction channel 116 also extends through the body 108 from the proximal end 120 to the distal end 122 along a third axis D. The third axis D extends substantially parallel relative to the central axis C. The third axis D may be distanced from the central axis C at a distance ranging, for example, between 4.0 mm and 6.0 mm. In one particular embodiment, the third axis D may be distanced from the central axis C by a distance of 5.0 mm. It will be understood by those of skill in the art, however, that the distance of the axis D from the central axis C may vary, as desired. For example, the axis D may be distanced from the central axis C by a distance of up to 15 mm.

Each of the central channel 110 and the first, second and third corrections channels 112, 114, 116 is sized and shaped to receive a guide wire therein. In one embodiment, the channels 110-116 are sized and shaped to receive guide wires having a diameter ranging from 2.5 mm to 3.0 mm. In a particular embodiment, the channels 110-116 are sized to receive guide wires having a 2.8 mm diameter. As will be described in greater detail below, the device 102 may be slid along an initially inserted first guide wire 104 with the first guide wire 104 received within the central channel 110. The second guide wire 106 may then be inserted into one of the first, second and third correction channels 112, 114, 116 to correct an initial placement of the first guide wire 104. The first and second correction channels 112, 114 extend along opposing sides of the body 108 so that, if an angulation of the second guide wire 106 relative to the first guide wire 104 is desired, the user may determine a direction in which it is desired to angulate the second guide wire 106 with respect to the first guide wire 104.

A size and shape of the body 108 may be defined via the central channel 110 and the first, second and third correction channels 112, 114, 116, tapering from the proximal end 120 to the distal end 122. Thus, smaller angulations of the first and second correction channels 112, 114 will produce a smaller taper while larger angulations will produce larger taper. A length of the body 108 may be selected so that the device 102 may be inserted through tissue and into a living body so that the distal end 122 may contact the bone while the handle portion 118, which is connected to the proximal end 120, extends outside of the body. In addition, a length of the channels 110-116 should be long enough to provide precision during insertion of the guide wires along the axes A-D. In an exemplary embodiment, a length of the body 108 may range from between 100 and 200 mm. In a specific embodiment, the body 108 of the correction device 102 may have a length of approximately 142 mm.

The handle portion 118 optionally includes first and second winged handles 124, 126, respectively, each extending laterally from the proximal end 120 of the body 108 at an angle relative to a longitudinal axis of the device 102. The first and second winged handles 124, 126 extend from substantially opposing sides of the body 108. In one embodiment, the first winged handle 124 extends from the side of the body 108 including the first correction channel 112 and the second winged handle 126 extends from the side of the body 108 including the second correction channel 114. An angle of the first and second winged handles 124, 126 relative to the longitudinal axis of the device 102 is selected to facilitate ease of gripping of at least one of the first and second handles 124, 126. Thus, regardless of an orientation of the device 102 relative to the bone, the user will have at least one handle to grip while inserting the second guide wire 106 through one of the first, second and third correction channels 112, 114, 116.

According to an exemplary surgical method using the system 100, the first guide wire 104 is inserted along an axis of the femoral neck and into the femoral head. The first guide wire 104 may be inserted into the femoral head using an angled guide, which permits insertion of the first guide wire 104 at a predetermined angle relative to a longitudinal axis of the femur. Once the first guide wire 104 has been inserted into the bone, the user may take an image scan (e.g., x-ray) of the proximal portion of the femur to determine whether a correction is required. In most cases, it is desirable for the guide wire to be inserted along a central axis of the femoral neck. Thus, if it is determined from the image scan that the first guide wire 104 is not positioned as desired (e.g., centrally and inline within the femoral neck and head), the user may determine that correction is required. Based on the image scan, the user may also determine a desired corrected path of the guide wire. For example, the user may determine whether the guide wire should be angulated in an anterior or posterior direction relative to the initially placed first guide wire 104, or whether it is desired for the guide wire to extend parallel to the initially placed first guide wire 104 but offset laterally therefrom.

The device 102 is slid along the first guide wire 104 with the first guide wire 104 received within the central channel 110 until the distal end 122 contacts the bone. The user may rotate the device 102 about the first guide wire 104 until an entry point of the second guide wire 106 (e.g., a distal opening of a selected one of the first, second and third correction channels 112, 114, 116 through which the second guide wire 106 will be inserted) is in alignment with the desired corrected path. The user then grips one of the first and second handles 124, 126 to hold the device 102 against the bone, in the desired orientation, while inserting the second guide wire 106 through the selected one of the first, second and third correction channels 112, 114, 116, respectively. As would be understood by those skilled in the art, the user determines which of the first, second and third correction channels 112, 114, 116 to use based on the determined desired corrected path. The second guide wire 106 is inserted into the bone via the selected correction channel and the new entry point along the desired corrected path, in alignment with one of the first, second and third axes A, B, D. As would be understood by those skilled in the art, after insertion of the second guide wire 106, the first guide wire 104 and the device 102 may be removed from the patient body.

If so desired, another image scan of the proximal femur may be taken to confirm that the second guide wire is in the desired position within the bone. In the case that the second guide wire 106 also requires correction, the above-described process may be repeated by sliding the device 102 over the second guide wire 106 so that the second guide wire 106 is received within the central channel 110. A third guide wire may be inserted through one of the first, second and third correction channels 112, 114, 116 along a desired corrected path.

Alternatively, in some cases, the desired corrected path may have a greater angulation relative to the first guide wire 104 and/or is at a greater distance than is permitted via the device 102. For example, the axes A and B may extend at a 5° angle relative to the axis C, while the desired path is 10° relative to the first guide wire 104. In such cases, the above-described process may be repeated using additional guide wires until a path of insertion of a guide wire substantially corresponds to the desired corrected path.

Although the exemplary embodiment describes and shows three correction channels 112-116, it will be understood by those of skill in the art that the device 102 may include additional channels to provide additional angulation and/or distance options. Additional channels, however, may increase a size of the body 108 of the device 102.

Figure 7:
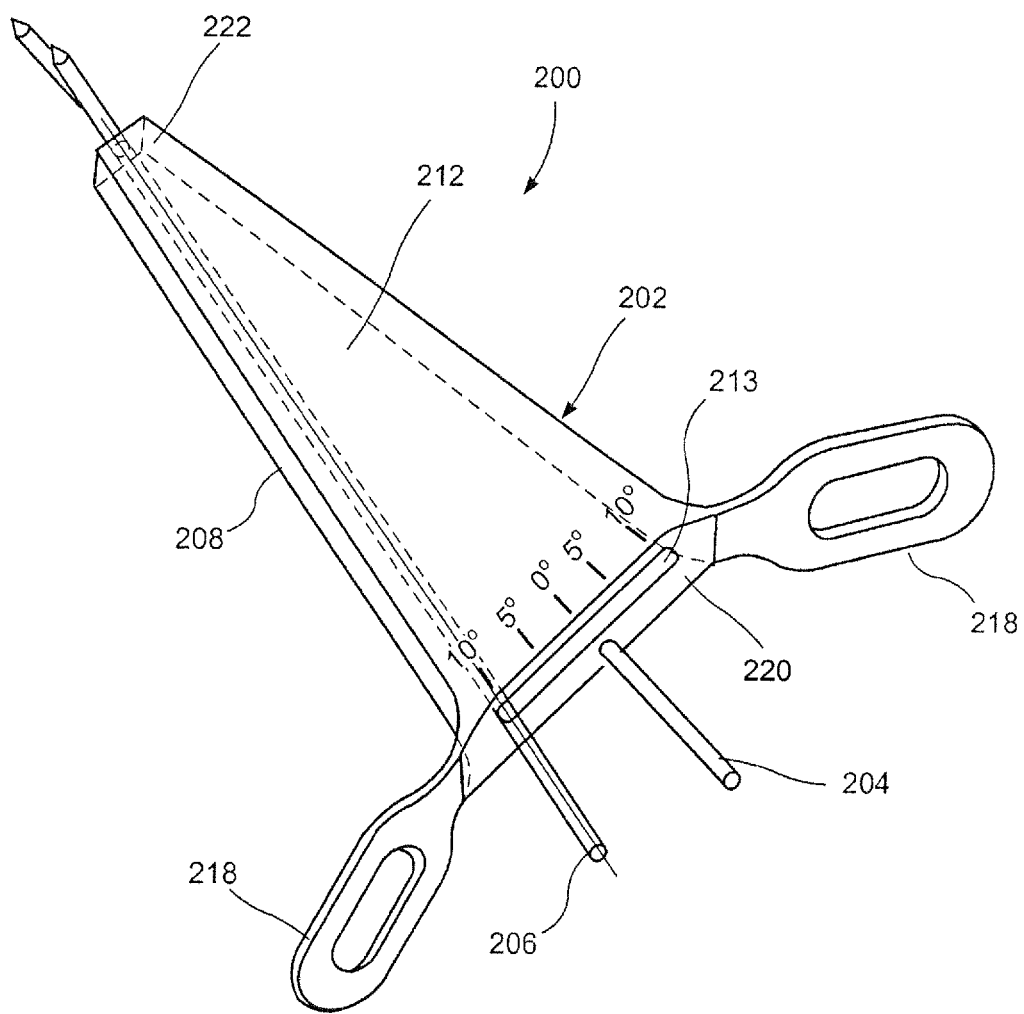
FIG. 7 shows a perspective view of a system according to another exemplary embodiment of the present disclosure.

As shown in FIG. 7, a system 200 according to another exemplary embodiment of the present disclosure may be substantially similar to the system 100, comprising a device 202 for correcting an initial placement of a first guide wire 204 by permitting insertion of a second guide wire 206 at an angle relative to and/or at a distance from the first guide wire 204. The device 202 may be substantially similar to the device 102. However, whereas the device 102 provides a plurality of correction channels 112-116, each of which are specifically sized and shaped to correspond to a single guide wire so that the second guide wire 106 may be inserted into the bone only at specific, pre-determined angles/distances relative to the first guide wire 104, the device 202 includes a slotted correction channel 212 which permits insertion of a guide wire therethrough along an axis angled relative to an axis C of a central channel 210 of the device 202, within a permitted range of angulations.

In particular, the device 202 includes a body 208 extending from a proximal end 220 to a distal end 222, a handle portion 218 extending from the proximal end 220 the body 208. The device 202 includes the central channel 210 extending through the body 208 from the proximal end 220 to the distal end 222 for receiving the first guide wire 204. The slotted correction channel 212 also extends through the body 208 from the proximal end 220 to the distal end 222. The slotted correction channel 212 tapers from the proximal end 220 toward the distal end 222 so that a proximal opening 213 thereof is slotted (i.e., elongated) to permit insertion of the second guide wire 206 therethrough, within a permitted range of angulations.

In one example, the slotted correction channel 212 may permit insertion of the second guide wire 206 therethrough at an angle ranging from between −10° to 10° relative to the central axis C. It will be understood by those of skill in the art, however, that this permitted range of angulation may vary, as desired. The body 208 may be marked with the permitted range of angulations so that a user may insert the second guide wire 206 through the slotted correction channel 212 in alignment with a marking showing the desired angulation of the second guide wire 206. The second guide wire 206 may be inserted into the bone at an angle relative to the first guide wire 204 (which is received within the central channel 210) or parallel to the first guide wire 204. To insert the second guide wire 206 parallel to the first guide wire 204, the second guide wire 206 may be inserted through the slotted channel 212 in alignment with a 0° marker shown on the body 208.

Although the device 202 of the system 200 is shown and described as including a single slotted channel 212, it will be understood by those of skill in the art that a device according to the present disclosure may include more than one slotted channel providing a predetermined range of angulations of a guide wire inserted therethrough. It will also be understood by those of skill in the art that a device according to the present disclosure may also include a combination of at least one slotted channel, as described above with respect to the device 202, and at least one of the correction channels described above with respect to the device 102.

The system 200 may be used in a manner substantially similar to the device 100. In particular, the device 202 may be slid over an initially placed first guide wire 204 such that the first guide wire 204 is received within the central channel 210. Based on an image scan of the proximal femur (or other portion of the bone through which the guide wire is inserted) the user may determine a desired corrected path for the second guide wire 206. The second guide wire 206 may be inserted through the slotted channel 212 and into the bone along in alignment with a marking corresponding to the desired corrected path.

Figure 8:
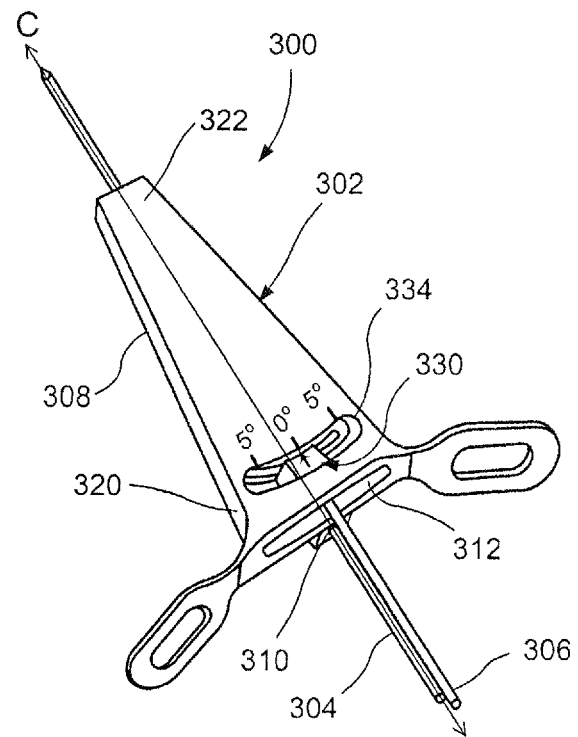
FIG. 8 shows a perspective view of a system according to a further exemplary embodiment of the system shown in FIG. 7.

As shown in FIG. 8, a system 300 according to a further exemplary embodiment of the present disclosure may be substantially similar to the system 200 described above, comprising a device 302 for correcting an initial placement of a first guide wire 304 by permitting insertion of a second guide wire 306 at an angle relative to and/or at a distance from the first guide wire 304. Similarly to the device 202, the device 302 includes a central channel 310 and a slotted channel 312 extending longitudinally through a body 308 of the device 302 from a proximal end 320 of the body 308 to a distal end 322 of the body 308. The slotted channel 312 is substantially similar to the slotted channel 212, permitting insertion therethrough of the second guide wire 306 at a desired angle within a permitted range of angulations relative to a central axis C of the central channel 310, in which the first guide wire 304 is received. The device 302, however, further includes a slider 330 movably received within the slotted channel 312. The slider 330 includes an opening extending longitudinally therethrough. The opening is sized and shaped to receive a guide wire therethrough. The slider 330 may be moved laterally within the slotted channel 312 so that the slider 330 may be positioned in alignment with a desired angle (corresponding to a desired correction path) within the permitted range of angulations. The slider 330 may provide a greater precision for the insertion of the second guide wire 306 along the desired correction path.

The slider 330 may be slidably housed within a correspondingly sized and shaped groove 334 extending laterally through the body 308 in communication with the slotted channel 312. The groove 334 houses the slider 330 such that a portion thereof is accessible to the user so that the user may slide the slider 330 laterally relative to the body 308 into alignment with, for example, a marking showing the desired angle within the permitted range of angulations. The slider 330 may include features preventing the slider 330 from moving during insertion of the second guide wire 306. For example, the slider 330 may be friction fit within the groove 334 and/or include an engaging feature which permit the slider 330 to be clicked or snapped into a desired one of a plurality of correspondingly sized and shaped engaging features of the groove 334. The correspondingly sized and shaped engaging features of the groove 334 may permit the slide 330 to be fixed at the desired position relative to the body 308.

Figure 9:
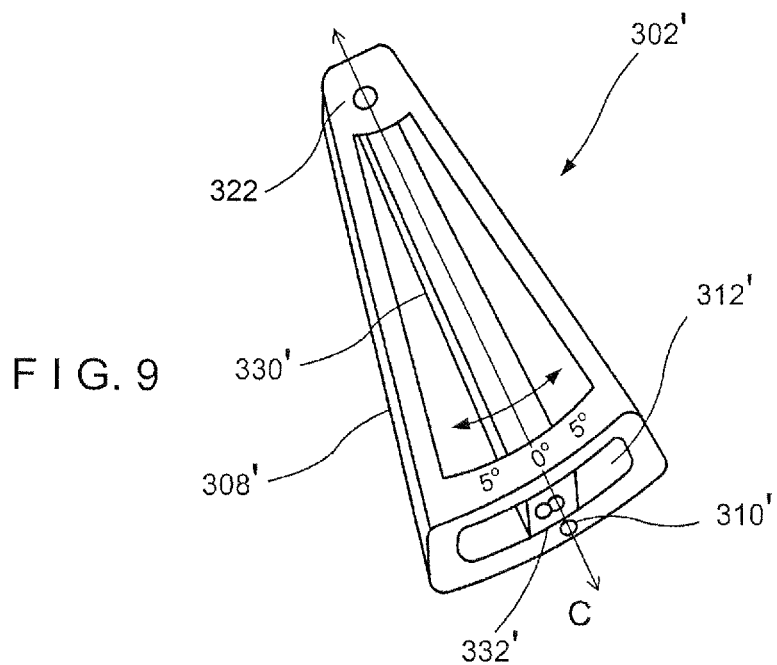
FIG. 9 shows a perspective view of a device according to an alternate embodiment of the system shown in FIG. 8.

According to an alternate embodiment, as shown in FIG. 9, rather than a slider received within a laterally extending groove, a device 302' may include a longitudinally extending slider 330' received within a slotted channel 312' and pivotally coupled to a distal end 322' of a body 308' of the device 302'. The slider 330' includes an alignment channel 332' extending longitudinally therethrough, the alignment channel 332' sized and shaped to receive a guide wire therein. The slider 330' may be pivoted into alignment with a marking showing a desired angulation (corresponding to a desired correction path) within a permitted range of angulations relative to a central axis C of a central channel 310' of the device 302' to provide greater precision of insertion along the desired correction path.

The devices 302, 302' may be used in a manner substantially similarly to the devices 102, 202 described above. In particular, the device 302 (or 302') may be slid along an initially placed first guide wire 304. The slider 330 is moved into alignment with a desired correction path of the guide wire so that the second guide wire 306 may be guided through the opening thereof and into the bone.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A method for correcting a guide wire placement in a bone, comprising:
   inserting a first guide wire into a bone;
   determining a desired corrected placement of the first guide wire;
   inserting the first guide wire into an initial channel of a device along an initial axis;
   sliding the device along the first guide wire until a distal end thereof abuts a surface of the bone; and
   inserting a second guide wire through a correction channel of the device, the correction channel being oriented, when the device is received over the first guide wire, to direct the second guide wire into the bone along a correction axis of insertion corresponding to the desired corrected placement of the first guide wire, the correction axis of insertion of the second guide wire being selected between an axis that is angled at a fixed angle relative to the initial axis and an axis that is parallel to the initial axis.

2. The method of claim 1, wherein the correction channel extends through the device along one of a first axis angled relative to the initial axis, a second axis angled relative to the initial axis where the second axis is on a side of the initial axis opposite the first axis, and a third axis parallel to the initial axis.

3. The method of claim 2, wherein the desired corrected placement of the first guide wire is determined based on an image of the bone into which the first guide wire has been inserted, the method further comprising inserting a third guide wire through the device along another one of the first, second and third axes to further correct a placement of the first guide wire.

4. The method of claim 1, wherein the device further includes a handle portion extending from a proximal end thereof, the handle portion includes a pair of wings extending laterally from the proximal end at an angle relative to a longitudinal axis of a body of the device, each of the wings extending from sides of the body on opposite sides of the initial channel.

5. The method of claim 1, further comprising:
   imaging the bone to confirm a desired correct placement of the second guide wire.

6. The method of claim 1, further comprising:
   determining a desired corrected placement of the second guide wire;
   inserting the second guide wire into the initial channel of the device;
   sliding the device along the second guide wire until the distal end thereof abuts the surface of the bone; and
   inserting a third guide wire through the correction channel of the device in accord with the desired corrected placement of the second guide wire.

7. The method of claim 6, further comprising:
   imaging the bone to confirm a desired correct placement of the third guide wire.

8. The method of claim 1, wherein a diameter of the correction channel is slightly greater than a diameter of the second guide wire.

9. The method of claim 1, wherein the correction channel tapers from a proximal end to the distal end of the device so that the second guide wire is receivable therein at a desired angle relative to the initial axis, within a permitted range of angulations.

10. The method of claim 9, wherein the device includes markings showing angles relative to the axis of the initial channel within the permitted range of angulations.

11. The method of claim 1, wherein the correction channel tapers from a proximal end to the distal end of the device so that a longitudinally extending slider is receivable therein at a desired angle relative to the initial axis, within a permitted range of angulations, the slider pivotably coupled to the distal end of the device and including an alignment channel extending longitudinally therethrough, the alignment channel sized and shaped to receive the second guide wire therein.

12. The method of claim 11, further comprising moving the slider along the correction channel so that an axis of the alignment channel of the slider aligns with the desired corrected placement of the first guide wire.

13. The method of claim 11, wherein the slider includes an engaging feature engageable with a plurality of correspondingly sized and shaped engaging features of an opening groove at a proximal end of the correction channel.

14. The method of claim 13, further comprising aligning the engaging feature of the slider with one of the engaging features of the groove to fix the slider at the desired angle of insertion.

15. The method of claim 1, wherein an axis of the correction channel is angled relative to the initial axis at an angle ranging from between 5 and 10 degrees.

16. The method of claim 1, wherein a length of the device is selected so that, when the device is slid along the first guide wire until the distal end thereof abuts the surface of the bone, the proximal end of the device extends proximally to be accessible to a user.

17. A method for correcting a guide wire placement in a bone, comprising:
inserting a first guide wire into a bone;
determining a desired corrected placement of the first guide wire;
inserting the first guide wire into an initial channel of a device along an initial axis;
sliding the device along the first guide wire until a distal end thereof abuts a surface of the bone;
inserting a second guide wire through a correction channel of the device, the correction channel being oriented, when the device is received over the first guide wire, to direct the second guide wire into the bone along a correction axis of insertion corresponding to the desired corrected placement of the first guide wire, the correction axis of insertion of the second guide wire being selected between an axis that is angled relative to the initial axis and an axis that is parallel to the initial axis; and
moving a slider so that an opening of the slider is aligned with a desired angle of insertion of the second guide wire through the correction channel, the slider slidably housed within a correspondingly sized and shaped groove extending laterally through the device in communication with the correction channel.

18. The method of claim 17, wherein the slider includes an engaging feature engageable with a plurality of correspondingly sized and shaped engaging features of the groove.

19. The method of claim 18, further comprising aligning the engaging feature of the slider with one of the engaging features of the groove to fix the slider at the desired angle of insertion.

20. A method for correcting a guide wire placement in a bone, comprising:
inserting a first guide wire into a bone;
determining a desired corrected placement of the first guide wire;
inserting the first guide wire into an initial channel of a device along an initial axis, the device containing a plurality of guide wire markings and a correction channel tapering from a proximal end to a distal end of the device so that a second guide wire is receivable therein at a desired angle relative to the initial axis, within a permitted range of angulations;
sliding the device along the first guide wire until a distal end thereof abuts a surface of the bone;
moving a slider so that an opening of the slider is aligned with a desired angle of insertion of the second guide wire through the correction channel, the slider slidably housed within a correspondingly sized and shaped groove extending laterally through the device in communication with the correction channel; and
inserting the second guide wire through the device in alignment with a first one of the guide wire markings corresponding to the desired corrected placement of the first guide wire.

21. The method of claim 20, further comprising:
imaging the bone to confirm a desired correct placement of the second guide wire.

22. The method of claim 20, wherein the desired corrected placement of the first guide wire is determined based on an image of the bone into which the first guide wire has been inserted, the method further comprising inserting a third guide wire through the correction channel of the device in alignment with one of the plurality of guide wire markings to further correct a placement of the first guide wire.

23. The method of claim 22, further comprising:
imaging the bone to confirm a desired correct placement of the third guide wire.

24. The method of claim 20, wherein a first one of the guide wire markings corresponds to an angular separation from the initial channel and a second one of the guide wire markings corresponds to a lateral separation from the initial channel.

25. The method of claim 20, wherein the device further includes a handle portion extending from a proximal end thereof, the handle portion includes a pair of wings extending laterally from the proximal end at an angle relative to a longitudinal axis of a body of the device, each of the wings extending from sides of the body on opposite sides of the initial channel.

* * * * *